United States Patent

Riondel et al.

[11] Patent Number: 5,912,383
[45] Date of Patent: *Jun. 15, 1999

[54] STABILIZED AQUEOUS SOLUTIONS OF UNSATURATED QUATERNARY AMMONIUM SALTS

[75] Inventors: Alain Riondel, Forbach; Robert Legros, Monceaux, both of France

[73] Assignee: Elf Atochem S.A., France

[ * ] Notice: This patent is subject to a terminal disclaimer.

[21] Appl. No.: 08/889,369

[22] Filed: Jul. 8, 1997

[30] Foreign Application Priority Data

Jul. 8, 1996 [FR] France ................... 96 08476

[51] Int. Cl.[6] ............................. C07C 233/89
[52] U.S. Cl. ........................... 560/222; 560/221
[58] Field of Search ................... 560/222, 221

[56] References Cited

FOREIGN PATENT DOCUMENTS

| 0 250 325 | 12/1987 | European Pat. Off. . |
| 0 273 415 | 7/1988 | European Pat. Off. . |
| 0 302 122 | 2/1989 | European Pat. Off. . |
| 2 642 424 | 3/1990 | France . |

OTHER PUBLICATIONS

Chemical Abstracts, vol. 97, No. 20, Abstract No. 163659, Nov. 15, 1982, Columbus, OH (USA).
Database WPI, Section Ch, Wk. 9349, Abstract No. 93–392677, Nov. 9, 1993, Derwent Publications Ltd., London (GB).

*Primary Examiner*—Robert Gerstl
*Attorney, Agent, or Firm*—Millen, White, Zelano, & Branigan, P.C.

[57] ABSTRACT

A description is given of a stabilized aqueous solution of unsaturated quaternary ammonium salt(s) (I), having been obtained by reaction, in the presence of water, of N,N-dimethylaminoethyl (meth)acrylate (II) with a quaternizing agent (III), at least one stabilizing agent having been used in combination with the monomer (II). This aqueous solution contains at least one sequestering agent for metals chosen from diethylenetriaminepentaacetic acid, the pentasodium salt of diethylenetriaminepentaacetic acid, N-(hydroxyethyl) ethylenediaminetriacetic acid and the trisodium salt of N-(hydroxyethyl)ethylenediaminetriacetic acid.

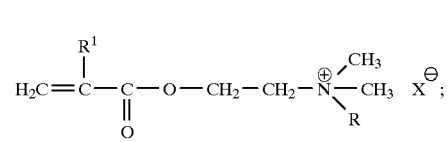

(I)

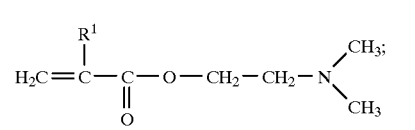

(II)

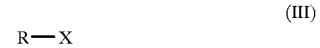

(III)

$R^1$=H or $CH_3$; R=methyl or benzyl; X=Cl, Br or $CH_3$—$SO_4$.

20 Claims, No Drawings

STABILIZED AQUEOUS SOLUTIONS OF UNSATURATED QUATERNARY AMMONIUM SALTS

CROSS-REFERENCE TO RELATED APPLICATION

This application is related to a concurrently filed application entitled, "PROCESS FOR THE MANUFACTURE OF AQUEOUS SOLUTIONS OF UNSATURATED QUATERNARY AMMONIUM SALTS", Ser. No. 08/889,320, (Attorney Docket No. ATOCM 92), based on French Application No. 96/08477 filed Jul. 8, 1996, by Alain RIONDEL.

FIELD OF THE INVENTION

The present invention relates to aqueous solutions of unsaturated quaternary ammonium salts (hereinafter known as quaternary salts), corresponding to the following formula

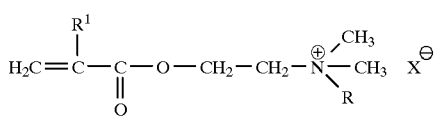
(I)

in which:
R$^1$ represents a hydrogen atom or a methyl radical;
R represents a methyl radical or a benzyl radical;
X is chosen from Cl, Br, I or CH$_3$—SO$_4$, the quaternary salts (I) having been obtained by reaction, in the presence of water, of N,N-dimethylaminoethyl (meth)acrylate of formula (II):

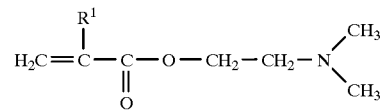
(II)

in which R$^1$ is as defined above, with a quaternizing agent of formula (III):

R—X (III)

in which R and X are also as defined above.

BACKGROUND OF THE INVENTION

Use is made of aqueous solutions of quaternary salts (I) to prepare polymers intended to act as flocculants in water treatment.

The main problems which are posed during the synthesis of the quaternary salts (I) are, on the one hand, the sensitivity to water of the monomers (II) and, on the other hand, the risks of polymerization of the reaction mixture in the reactor and those of the quaternary salts (I) on storage.

Japanese Patent Applications JP-A-57 109 747 and JP-A-57 109 749 describe a process for stabilizing salts of formula (I). This process consists in adding, to these salts, at least one chelating agent which can be an aminocarboxylic acid and respectively a nitrose compound or a compound of quinone type. In practice, ethylenediaminetetraacetic acid (EDTA) and the trisodium salt of nitrilotriacetic acid have been experimented with as aminocarboxylic acid, either with a nitroso compound or with benzoquinone, in order to stabilize an aqueous methacryloyloxyethyltrimethylammonium chloride solution.

EDTA is also the only sequestering agent cited in European Patent Application EP-A-302 122, which describes a process for the preparation of unsaturated quaternary ammonium salts by quaternization in a medium composed of water and an aprotic organic solvent.

SUMMARY OF THE INVENTION

It has now been discovered that the use of specific sequestering agents, belonging to the family of aminocarboxylic acids and their salts, makes it possible to obtain solutions of salts having excellent stability at room temperature.

The subject of the present invention is thus first a stabilized aqueous solution of at least one unsaturated quaternary ammonium salt, corresponding to the formula (I) as defined above and having been obtained by the reaction of a monomer (II) and of a quaternizing agent (III), as indicated above, the said aqueous solution containing at least one stabilizing agent in combination with the monomer (II) and additionally containing at least one sequestering agent for metals, characterized in that the sequestering agent for metals is chosen from diethylenetriaminepentaacetic acid, the pentasodium salt of diethylenetriaminepentaacetic acid, N-(hydroxyethyl)ethylenediaminetriacetic acid and the trisodium salt of N-(hydroxyethyl)ethylenediaminetriacetic acid.

The content of sequestering agent(s) according to the invention is, generally, from approximately 1 to 100 ppm with respect to the aqueous solution of quaternary salt of formula (I). The sequestering agents are preferentially added to the monomer (II) at the beginning of the reaction.

The stabilizing agents are chosen in particular from 3,5-di-tert-butyl-4-hydroxytoluene, hydroquinone methyl ether, hydroquinone, catechol, tert-butylcatechol and their mixtures.

The content of stabilizing agent(s) is, in accordance with the present invention, from approximately 20 to 1200 ppm with respect to the aqueous solution of quaternary salt of formula (I).

The aqueous quaternary salt solutions according to the invention are solutions containing concentrations in particular of approximately 50 to 85% by weight of quaternary salts (I) in water.

Another subject of the present invention is a process for the manufacture of a stabilized aqueous solution of unsaturated quaternary ammonium salt, corresponding to the formula (I) as defined above, from at least one (meth)acrylic monomer and from at least one quaternizing agent of the formulae (II) and (III) respectively, also as defined above, in the presence of at least one stabilizing agent in combination with the monomer (II) introduced at the beginning of the reaction, characterized in that at least one sequestering agent for metals is added to the monomer (II) at the beginning of the reaction and/or to the aqueous solution obtained, the sequestering agent for metals being chosen from diethylenetriaminepentaacetic acid, the pentasodium salt of diethylenetriaminepentaacetic acid, N-(hydroxyethyl)ethylenediaminetriacetic acid and the trisodium salt of N-(hydroxyethyl)ethylenediaminetriacetic acid.

Examples of stabilizing agents and the preferred amounts of the latter, as well as those of the sequestering agents, have been indicated above.

Generally, the sequestering agents according to the invention are added in the form of an aqueous solution, because they are generally available in this form. Thus, the pentasodium salt of diethylenetriaminepentaacetic acid, sold under the name Versenex 80, is provided in the form of an approximately 40% by weight aqueous solution.

A particularly preferred application of the process according to the invention is to that which forms the subject of European Patent EP-B-0 250 325. To this end:

(a) the (meth)acrylic monomer (II) is reacted, in a closed reactor, with 5 to 20% by weight of the amount of quaternizing agent (III) necessary for the reaction, this quaternizing agent being introduced continuously into the reactor; or (a') the (meth)acrylic monomer (II) and 5 to 20% by weight of an aqueous solution of quaternary salt (I) with respect to the weight of the (meth)acrylic monomers (II) comprising from 50 to 85% by weight of quaternary salt are introduced into a closed reactor;

(b) water and the remainder of the quaternizing agent (III) are then continuously added until the desired concentration of quaternary ammonium salt (I) in the water is obtained;

(c) the temperature is maintained, during the stages (a) or (a') and (b), at a value of between 30 and 60° C.; and (d) during the stages (a) or (a') and (b) and at the approach of the end of the reaction in particular, a stream of oxygen-containing gas is maintained in the reaction mixture, such that the ratio by volume of total gas at the outlet of a reactor to the oxygen introduced at the inlet of this same reactor is less than 100/1.

During the reaction, a ratio by volume of gas exiting from the reactor to the oxygen introduced at the inlet of this reactor is preferably set which is less than 50/1.

With the aim of avoiding supersaturation of the reaction mixture with quaternary salt (I), a molar ratio of introduction of water to the quaternizing agent (III) is set during the stage (b) which is between 2.2 and 3.7.

Preferably, during the stages (a) or (a') and (b), a temperature of between 45° C. and 55° C. is maintained.

Preferably again, during the stage (a) or (a'), approximately 10% by weight respectively of quaternizing agent (III) or of an aqueous solution of quaternary salt (I) comprising 50 to 85% by weight of quaternary salt are introduced.

The process according to the invention is preferably carried out at a pressure of between atmospheric pressure and 1.6 bar in absolute pressure.

When the quaternizing agent (III) is a volatile compound which is gaseous at the reaction temperature, the introduction of the quaternizing agent during the reaction is carried out so as to limit its losses into the gas vents. The losses are thus maintained at less than 10% (molar) of stoichiometry.

The outlet gas of the reactor is then conveyed to a treatment device which is targeted at ridding it of the traces of the quaternizing agent (III) which it contains, in particular in the case where the latter has a high vapour pressure or is volatile at the reaction temperature. The gas is preferably conveyed into a second reactor comprising (meth)acrylic monomer (II) in which the quaternizing agent (III) is trapped.

At the end of the reaction, the traces of quaternizing agent (III) dissolved in the reaction mixture are removed by flushing the latter with a high flow rate of oxygen-containing gas, for example air.

The quaternizing agents (III) which are highly suitable for the present invention are in particular halogenated hydrocarbons, such as methyl chloride, methyl bromide, methyl iodide, benzyl chloride, benzyl bromide and benzyl iodide, as well as dimethyl sulphate.

The examples which will follow, given by way of information, make it possible to better understand the invention. In these examples, the percentages shown are percentages by weight and the following abbreviations have been used:

DAMEA: N,N-dimethylaminoethyl acrylate

DAMEMA: N,N-dimethylaminoethyl methacrylate

Adamquat MC 80: 80% aqueous acryloyloxyethyltrimethylammonium chloride solution

Madquat MC 75: 75% aqueous methacryloyloxyethyltrimethylammonium chloride solution HQME: hydroquinone methyl ether Versenex 80: pentasodium salt of diethylenetriaminepentaacetic acid (aqueous solution containing 40% by weight of active material).

EXAMPLE 1

Preparation of Adamcuat MC 80

429 g of DAMEA, stabilized with 800 ppm of HQME, are charged to a jacketed reactor with stirring.

Throughout the duration of the reaction, i.e. 6 hours in total, the temperature is maintained at 47° C., the pressure is maintained at atmospheric and a continuous air flow rate of 0.4 Sl/h is maintained at the inlet of the reactor.

20 g of methyl chloride are introduced at a flow rate of 39 g/h for 0.5 hour, i.e. 12% of the total amount of $CH_3Cl$ necessary for the reaction, and then 143 g of water and 139 g of methyl chloride are introduced simultaneously at respective flow rates of 32 g/h and 39 g/h, i.e. a water/$CH_3Cl$ molar ratio of 2.3.

Air is then injected into the manufactured product at the rate of 5 Sl/h for 0.5 hour while hot. 720 g of Adamquat MC 80 are recovered.

The product thus obtained is stabilized with 10 ppm of Versenex 80.

The result of a stability test on storage of the aqueous salt solution obtained appears in the following Table 1. To carry out this stability test, a sealed test tube, 80% filled with Adamquat MC 80 doped with Versenex 80, is immersed in a thermostatically-controlled oil bath (temperature: 92° C.) and the effectiveness of the Versenex 80 is assessed by measuring the time before polymerization of the Adamquat MC 80.

EXAMPLE 2

The preparation is carried out as in Example 1, the Versenex 80 being replaced respectively by another sequestering agent as shown in Table 1.

The results are also reported in Table 1, at the same time as those of a control example without sequestering agent (Example 3) and of Comparative Examples 4 to 7 carried out with sequestering agents which do not belong to the invention.

TABLE 1

| Example | Sequestering agent | Time before polymerization (h) |
|---|---|---|
| 1 | Versenex 80 | 280 |
| 2 | Trisodium salt of N-(hydroxyethyl)-ethylenediaminetri-acetic acid | 300 |
| 3 (control) | Without sequestering agent | 3.25 |
| 4 (comparative) | Poly(acrylic acid) | 1 |
| 5 (comparative) | Poly(sodium acrylate) | 2 |
| 6 (comparative) | Tetrasodium salt of ethylenediaminetetra-acetic acid | 72 |
| 7 (comparative) | Ethylenediaminetetra-acetic acid | 154 |

EXAMPLE 8
Preparation of Madquat MC 75

314 g of DAMEMA, stabilized with 80 ppm of HQME and 10 ppm of Versenex 80 as a 40% aqueous solution, are charged to a jacketed reactor with stirring.

Throughout the duration of the reaction, i.e. 7.5 hours in total, the temperature is maintained at 50° C., the pressure is maintained at atmospheric and a continuous air flow rate of 0.4 Sl/h is maintained at the inlet of the reactor.

11 g of methyl chloride are introduced at a flow rate of 22 g/h for 0.5 hour, i.e. 10% of the total amount of $CH_3Cl$ necessary for the reaction, and then 138 g of water and the remaining methyl chloride, i.e. 100 g, are introduced simultaneously at respective flow rates of 21 g/h and 17 g/h, i.e. a water/$CH_3Cl$ molar ratio of 3.46.

At the approach of the end of the reaction, that is to say after approximately 6.5 hours, the methyl chloride flow rate is gradually reduced to 5 g/h.

Air is then injected into the manufactured product at the rate of 5 Sl/h for 0.5 hour while hot. 545 g of Madquat MC 75 are recovered.

For this Example 8 of the invention, the amounts of stabilizing agent and of sequestering agent used in combination with the Madquat MC 75 and the observations made with respect to the stability on storage of the aqueous solution obtained appear in the following Table 2. The results obtained with a Control Example 9, carried out in an identical way to Example 8 but without addition of sequestering agent, appear in parallel in the same table.

TABLE 2

| Example | Stabilizing agent (amount in ppm) | Sequestering agent (amount in ppm) | Observation of a polymerization at room temperature |
|---|---|---|---|
| 8 | HQME (45) | Versenex 80 (10) | No polymerization is observed after storing for one year |
| 9 (control) | HQME (45) | none | After storing for 48–72 hours |

EXAMPLE 10
Preparation of Madquat MC 75

The preparation is carried out as in Example 8 but using a different amount of stabilizing agent. The results are presented in Table 3, which is similar to Table 2, apart from the fact that the stability of the solution obtained at 70° C. has been shown therein in the last column. The results obtained in the case of a Control Example 11, carried out without sequestering agent, also appear in this Table 3.

TABLE 3

| Example | Stabilizing agent (amount in ppm) | Sequestering agent (amount in ppm) | Stability at 70° C. (hours) (*) |
|---|---|---|---|
| 10 | HQME (440) | Versenex 80 (10) | >24 |
| 11 (control) | HQME (1130) | None | 2 |

(*) Time before appearance of a positive polymers test

The preceding examples can be repeated with similar success by substituting the generically or specifically described reactants and/or operating conditions of this invention for those used in the preceding examples.

The entire disclosure of all applications, patents and publications, cited above, and of corresponding French application No. 96/08476, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. In a stabilized aqueous solution of at least one unsaturated quaternary ammonium salt(s), corresponding to the following:

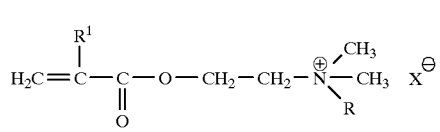

(I)

in which:
R¹ represents a hydrogen atom or a methyl radical;
R represents a methyl radical or a benzyl radical;
X is chosen from Cl, Br, I or $CH_3$—$SO_4$,
the quaternary salts (I) having been obtained by reaction, in the presence of water, of N,N-dimethylamino-ethyl (meth)acrylate of formula (II):

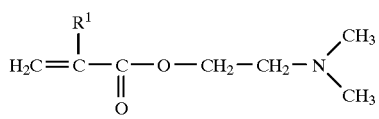

in which $R^1$ is as defined above,
with a quaternizing agent of formula (III):

R—X     (III)

in which R and X are also as defined above,
the said aqueous solution containing at least one stabilizing agent in combination with the monomer (II) and additionally containing at least one sequestering agent for metals, the improvement wherein the sequestering agent for metals is diethylenetriaminepentaacetic acid, the pentasodium salt of diethylenetriaminepentaacetic acid, N-(hydroxyethyl) ethylenediaminetriacetic acid or the trisodium salt of N-(hydroxyethyl)ethylene-diaminetriacetic acid.

2. An aqueous solution according to claim 1, wherein in that the content of sequestering agent(s) is from 1 to 100 ppm with respect to the aqueous solution of quaternary salt (I).

3. An aqueous solution according to claim 1, wherein the stabilizing agent is 3,5-di-tert-butyl-4-hydroxytoluene, hydroquinone methyl ether, hydroquinone, catechol, tert-butylcatechol or a mixture of said stabilizing agents.

4. An aqueous solution according to claims 1 the content of stabilizing agent(s) is from 20 to 1200 ppm with respect to the aqueous solution of quaternary salt (I).

5. An aqueous solution according to claim 1, wherein the concentration of the quaternary salt (I) is from 50 to 85% by weight.

6. In a process for the manufacture of a stabilized aqueous solution of unsaturated quaternary ammonium salt, corresponding to the formula (I) as defined in claim 1, from at least one (meth)acrylic monomer and from at least one quaternizing agent of the formulae (II) and (III) respectively, also as defined in claim 1, in the presence of at least one stabilizing agent in combination with the monomer (II) introduced at the beginning of the reaction, characterized in that at least one sequestering agent for metals is added to the monomer (II) at the beginning of the reaction and/or to the aqueous solution obtained, the improvement wherein the sequestering agent for metals is diethylenetriaminepentaacetic acid, the pentasodium salt of diethylenetriaminepentaacetic acid, N-(hydroxyethyl)-ethylenediaminetriacetic acid or the trisodium salt of N-(hydroxyethyl) ethylenediaminetriacetic acid.

7. A process according to claim 6, wherein the at least one sequestering agent is added in the form of an aqueous solution.

8. A process according to claim 6 wherein:
(a) the (meth)acrylic monomer (II) is reacted, in a closed reactor, with 5 to 20% by weight of the amount of quaternizing agent (III) necessary for the reaction, this quaternizing agent being introduced continuously into the reactor; or
(a') the (meth)acrylic monomer (II) and 5 to 20% by weight of an aqueous solution of quaternary salt (I) with respect to the weight of the (meth)acrylic monomers (II) comprising from 50 to 85% by weight of quaternary salt are introduced into a closed reactor;
(b) water and the remainder of the quaternizing agent (III) are then continuously added until the desired concentration of quaternary ammonium salt (I) in the water is obtained;
(c) the temperature is maintained, during the stages (a) or (a') and (b), at a value of between 30 and 60° C.; and
(d) during the stages (a) or (a') and (b) and at the approach of the end of the reaction in particular, a stream of oxygen-containing gas is maintained in the reaction mixture, such that the ratio by volume of total gas at the outlet of a reactor to the oxygen introduced at the inlet of this same reactor is less than 100/1.

9. A process according to claim 8, wherein the reaction is carried out at an absolute pressure of between atmospheric pressure and 1.6 bar.

10. A process according to claim 8, further comprising conveying gas exiting from the reactor is to a second quaternization reactor comprising (meth)acrylic monomer so as to substantially eliminate traces of quaternizing agent R—X in the gas exiting from the reactor.

11. An aqueous solution according to claim 1, wherein the sequestering agent for metals is diethylenetriaminepentaacetic acid.

12. An aqueous solution according to claim 1, wherein the sequestering agent for metals is the pentasodium salt of diethylenetriaminepenta-acetic acid.

13. An aqueous solution according to claim 1, wherein the sequestering agent for metals is N-(hydroxyethyl) ethylenediaminetriacetic acid.

14. An aqueous solution according to claim 1, wherein the sequestering agent for metals is the trisodium salt of N-(hydroxyethyl)ethylenediaminetriacetic acid.

15. A process according to claim 6, wherein the sequestering agent for metals is diethylenetriaminepenta-acetic acid.

16. An process according to claim 6, wherein the sequestering agent for metals is the pentasodium salt of diethylenetriaminepenta-acetic acid.

17. A process according to claim 6, wherein the sequestering agent for metals is N-(hydroxyethyl) ethylenediaminetriacetic acid.

18. A process according to claim 6, wherein the sequestering agent for metals is the trisodium salt of N-(hydroxyethyl)ethylenediaminetriacetic acid.

19. In a stabilized aqueous solution of at least one unsaturated quaternary ammonium salt(s), corresponding to the following:

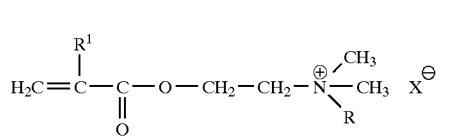

in which:
$R^1$ represents a hydrogen atom or a methyl radical;
R represents a methyl radical or a benzyl radical;
X is chosen from Cl, Br, I or $CH_3$—$SO_4$,
said aqueous solution containing at least one stabilizing agent in combination with at least one sequestering agent for metals, the improvement wherein the sequestering agent for metals is diethylenetriarninepentaacetic acid, the pentasodium salt of diethylenetriaminepenta-acetic acid, N-(hydroxyethyl)ethylenediaminetriacetic acid or the trisodium salt of N-(hydroxyethyl)ethylene-diaminetriacetic acid.

20. An aqueous solution according to claim 19, wherein the stabilizing agent is 3,5-di-tert-butyl-4-hydroxytoluene, hydroquinone methyl ether, hydroquinone, catechol, tertbutylcatechol or a mixture of said stabilizing agents.

* * * * *